(12) United States Patent
Ashman

(10) Patent No.: US 6,312,258 B1
(45) Date of Patent: *Nov. 6, 2001

(54) KIT FOR IMMEDIATE POST-EXTRACTION IMPLANTATION

(76) Inventor: Arthur Ashman, 153 Bayberry La., Westport, CT (US) 06880

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/378,127
(22) Filed: Aug. 19, 1999
(51) Int. Cl.⁷ .................................................. A61C 8/00
(52) U.S. Cl. .......................... 433/172; 206/369; 206/63.5
(58) Field of Search ............................. 433/172; 206/368, 206/369, 570, 63.5

(56) References Cited

U.S. PATENT DOCUMENTS

| | | | |
|---|---|---|---|
| 4,521,192 | * | 6/1985 | Linkow ................................ 433/173 |
| 4,828,113 | * | 5/1989 | Friedland et al. ..................... 206/570 |
| 4,973,168 | * | 11/1990 | Chan ..................................... 366/139 |
| 5,199,567 | * | 4/1993 | Discko, Jr. ............................ 206/369 |
| 5,312,254 | * | 5/1994 | Rosenlicht ............................ 433/173 |
| 5,582,299 | * | 12/1996 | Lazzara et al. ...................... 206/63.5 |
| 5,839,899 | * | 11/1998 | Robinson ............................. 433/215 |

* cited by examiner

Primary Examiner—John J. Wilson
Assistant Examiner—Melba Bumgarner
(74) Attorney, Agent, or Firm—Darby & Darby

(57) ABSTRACT

The present invention provides a kit system comprising a plurality of disposable kits, each kit being adapted for post-extraction dental implantation on a particular dental area. Each kit includes a dental implant of specified dimensions for a particular dental area of the mouth, a transfer coping attachable to the dental implant for creating an impression for making a model to produce a prosthetic tooth, bone graft material for filling the void area around a portion of the implant after implantation, burrs and bone expanders, and a portable housing for storing the dental implant, the transfer coping, the bone graft material, wound dressing and burrs and bone expanders. Each disposable kit includes indicia which uniquely identifies it with the particular dental area of use. The kit system may include a non-disposable instrument kit including a plurality of reusable and sterilizable tools such as insertion instruments, a scissor, and a suture holder, etc., for implementing post-extraction dental implantation, and a housing for storing the instruments. The invention further provides a method of using the kits.

12 Claims, 3 Drawing Sheets

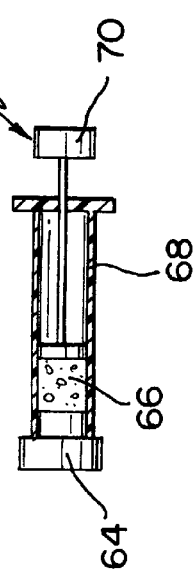
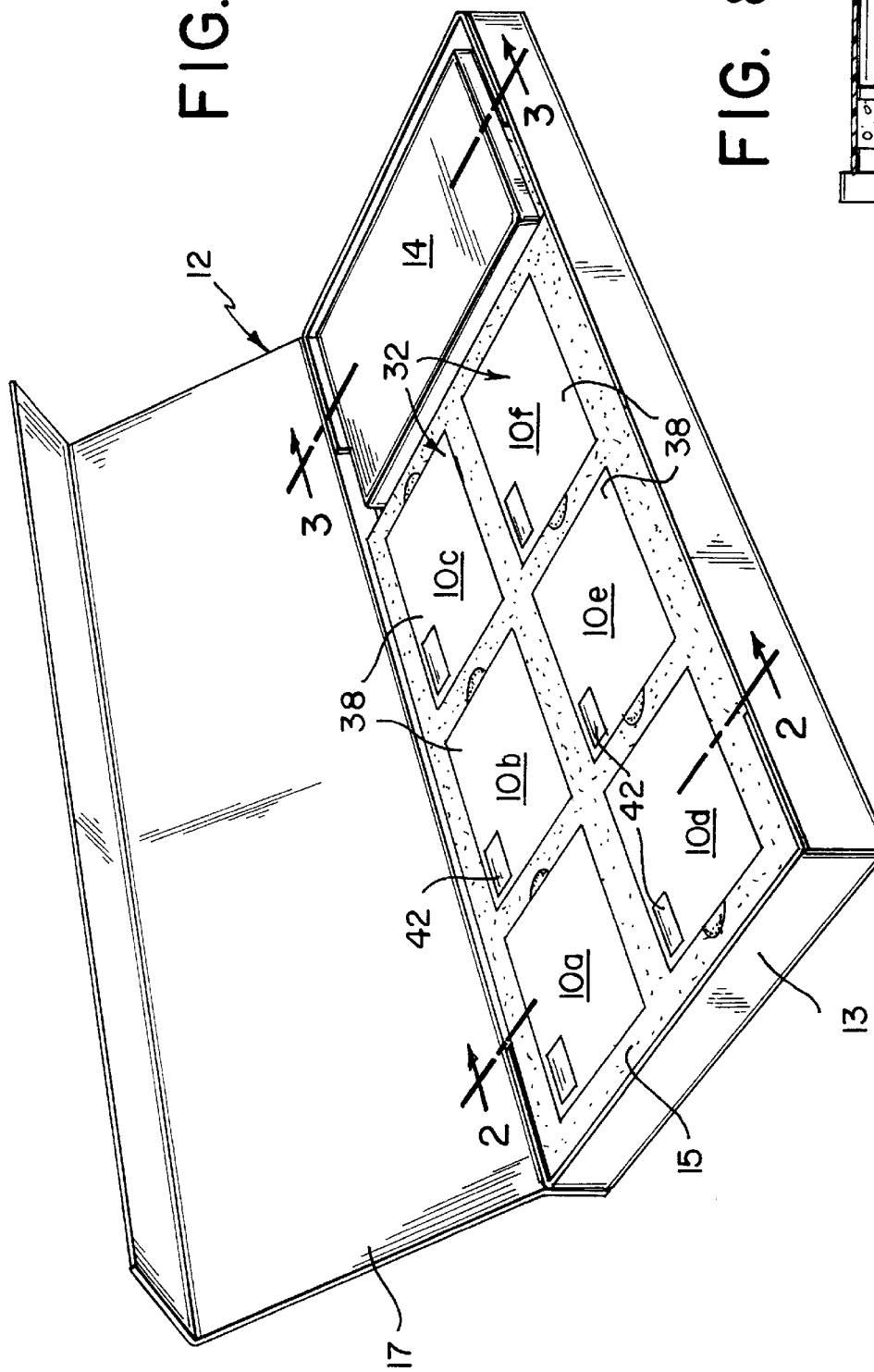

KIT FOR IMMEDIATE POST-EXTRACTION IMPLANTATION

BACKGROUND

The present invention relates generally to implant dentistry, and more particularly, to disposable implant kits, and a method of using the kits, unique to post-extraction implantation procedures for the various and different dental areas. In addition, the kit (s) can be utilized in other cranio-facial bone areas as well.

The process of fashioning a dental restoration for a patient usually involves several steps over a period of months. In a new method for placing an implant, typically after an extraction as shown and described in my copending application entitled METHOD AND APPARATUS FOR PERFORMING RIDGE PRESERVATION AND IMMEDIATE IMPLANT TREATMENT, filed $_{13}$____, an extraction socket in the alveolar bone of the patient is already opened to expose the bone. Rather than waiting months for this extraction socket to heal, it is possible to place an implant immediately after an extraction (before the bone has healed). A bore or extension hole is drilled at a base of the extraction socket 3 to 6 millimeters beyond the end of the socket (apically) to provide suitable space for insertion of a dental implant. The implant is then placed into the extraction socket using techniques and instrumentation appropriate to the type of implant being mounted. In most cases, a bone void will exist in the space between the upper portion of the implant and the exposed extraction socket. This bone void maybe "back filled" with bone graft material to promote integration ("osseointegration") between the implant and the bone, either with or without a membrane barrier depending upon the graft material used. For a single stage implant procedure, an abutment is installed in the implant during initial installation in the extraction socket. In a two stage procedure, the implant is submerged into the bone, and a healing cap or other structure is threaded into the top of the implant to prevent the migration of bone or soft tissue into the implant abutment space. New bone, however, may grow around and over the implant. If bone covers a submerged implant, it must be removed by a burr prior to installation of an abutment. A transfer coping is placed over the abutment to transfer an impression to resilient impression material from which a model is made of a previous edentulous site where the implant was installed. The artificial tooth is then mounted over the abutment structure in accordance with well known methods.

SUMMARY OF THE INVENTION

In accordance with the above objects and additional objects that will become apparent hereinafter, the present invention provides a disposable kit for implementing immediate post-extraction dental implantation. The kit includes a dental implant of a specified size for a particular dental area of the mouth; a transfer coping attachable to the dental implant for creating an immediate impression for making a model to produce a prosthetic tooth; bone graft material for filling the void around a portion of the implant after implantation; and a portable housing having a plurality of compartments for storing the dental implant, the transfer coping, and the bone graft material, etc. A wound dressing may also be stored in one of the compartments if desired (e.g., Biofoil®). The kit housing may include indicia corresponding to the target dental area.

The present invention also provides a kit system comprising a plurality of disposable kits, each kit being adapted for immediate post-extraction dental implantation on a particular dental area. Each kit includes a dental implant of a specified size for a particular dental area; a transfer coping attachable to the dental implant for creating an impression for making a model to produce a prosthetic tooth; a bone graft material for filling the void around a portion of the implant after implantation (where in some instances it may be necessary, because of a narrow or thin buccal or lingual plate housing the newly placed implant, to build out or expand the bucco-lingual diameter to thereby increase the amount of bone holding the implant under function); and a portable housing for storing the dental implant, the transfer coping, the bone graft material and the wound dressing, etc.

The kit system may include anon-disposable instrument kit including a plurality of reusable and sterilizable tools such as insertion instruments, a scissor, and a suture holder, etc., for implementing immediate post-extraction dental implantation, and a housing for storing the instruments.

The invention further provides a method for immediate post-extraction implantation of dental implants, comprising the steps of: immediately after extraction, removing from a kit adapted for a particular dental area of the mouth, a dental implant of specified dimensions for the particular dental area of the mouth, and inserting the dental implant into an extraction socket; removing a transfer coping from the kit, and attaching the transfer coping to the dental implant to make a model to produce a prosthetic tooth. The method may further comprise the step of removing a bone graft material from the kit and filling a void area around a portion of the implant after implantation.

BRIEF DESCRIPTION OF THE DRAWINGS

In accordance with the above, the present invention will now be described in detail with particular reference to the accompanying drawings.

FIG. 1 is an isometric view of a kit system for implementing post-extraction dental implantation in accordance with the present invention;

FIG. 8 is a detail view of a bone graft material syringe.

DETAILED DESCRIPTION OF THE PREFERRED EMBODIMENTS

Figure 6:
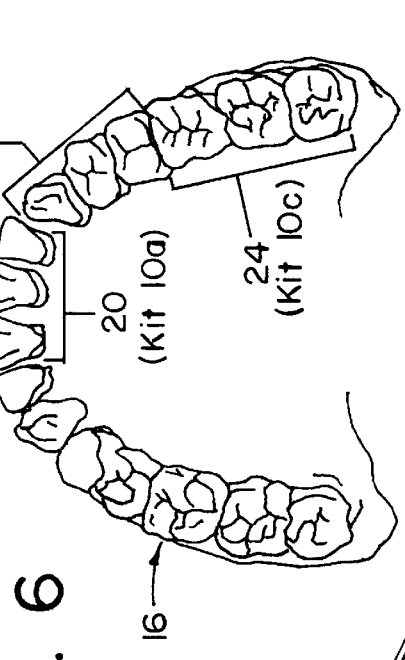
FIG. 6 is a view of the upper jawbone.
Figure 7:
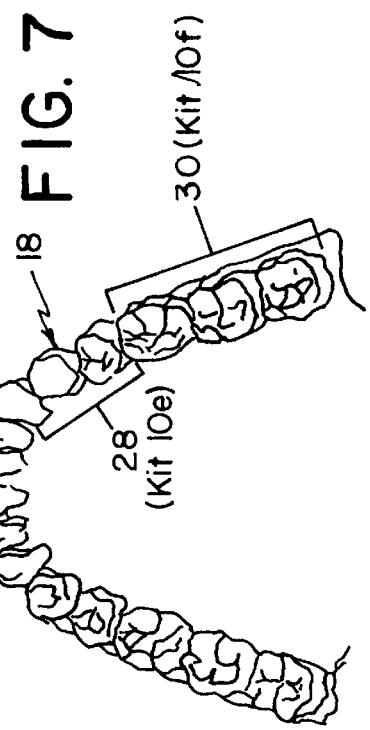
FIG. 7 is a view of the lower jawbone.

Referring to the several views of the drawings, there is shown a disposable kit system including a plurality of disposable kits and an instrument kit (FIG. 1), each disposable kit being adapted for post-extraction dental implantation on a particular dental area of the jawbones (FIGS. 6 and 7). The kits are preferably constructed from plastic materials, but it is to be understood that the use of other materials is within the scope of the invention.

Referring in particular to FIG. 1, a plurality of disposable kits 10a, 10b, 10c, 10d, 10e, 10f are schematically depicted as part of a kit system 12. A non-disposable instrument kit 14 is also provided as part of the kit system 12, and will be discussed in more detail below. Each disposable kit, which is generally referred to by the reference numeral 10 for clarity may come individually or collectively packaged, and includes a plurality of components used for post-extraction dental implantation on a particular dental area. FIGS. 6 and 7 of the jawbones show six dental areas, three in each of the upper 16 and lower 18 sets of teeth. The upper set 16 is segregated into the anterior (front) teeth 20, cuspids and bicuspids (upper jaw/maxilla) 22, and molars 24. The lower set 18 similarly comprises the anterior (front) teeth 26, cuspids and bicuspids (lower jaw/mandible) 28, and molars 30. Each kit 10 is uniquely associated with one of these dental areas. For convenience, kit 10a corresponds to the upper set anterior teeth 20, kit 10b corresponds to the upper cuspidslbicuspids 22, and kit 10c corresponds to the upper molars 24. Kit 10d corresponds to the lower set anterior teeth 26, kit 10e corresponds to the lower cuspids/bicuspids 28 and kit 10f corresponds to the lower molars 30.

The kit system 12 includes a housing 13 having a support material such as foam or the like 15 with a plurality of formed depressions for receiving the individual kits 10 and 14. A cover 17 is hingedly connected to the body of the housing 13 in a conventional manner. The depicted embodiment is only intended to be exemplary, as it is anticipated that the overall structure can take on a variety of forms within the scope of the invention, and that modifications thereof will be implemented by persons skilled in the art. It is to be understood that each kit maybe obtained individually, e.g., 10c alone or collectively with other kits in a kit system, 12.

Figure 2:
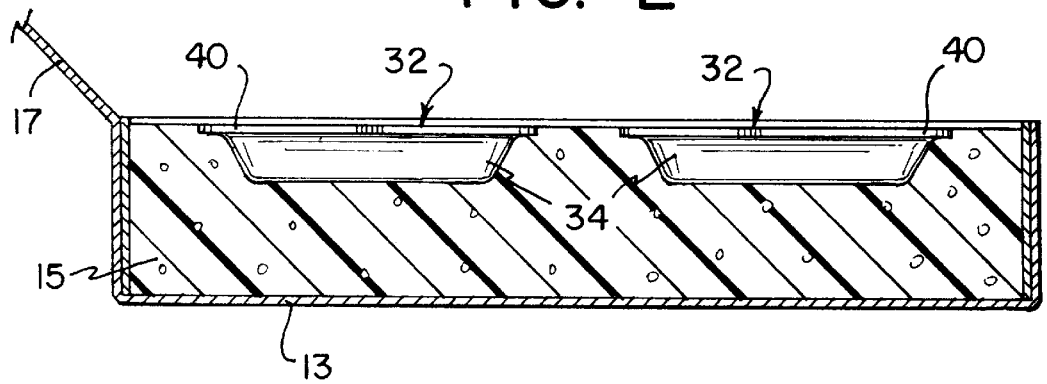
FIG. 2 is a sectional view of the kit system taken along lines 2—2 in FIG. 1.
Figure 3:
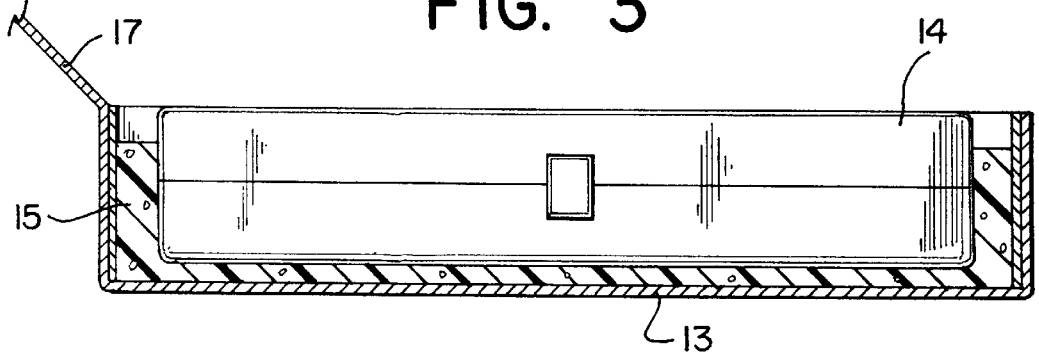
FIG. 3 is a sectional view of the kit system taken along lines 3—3 in FIG. 1.
Figure 4:
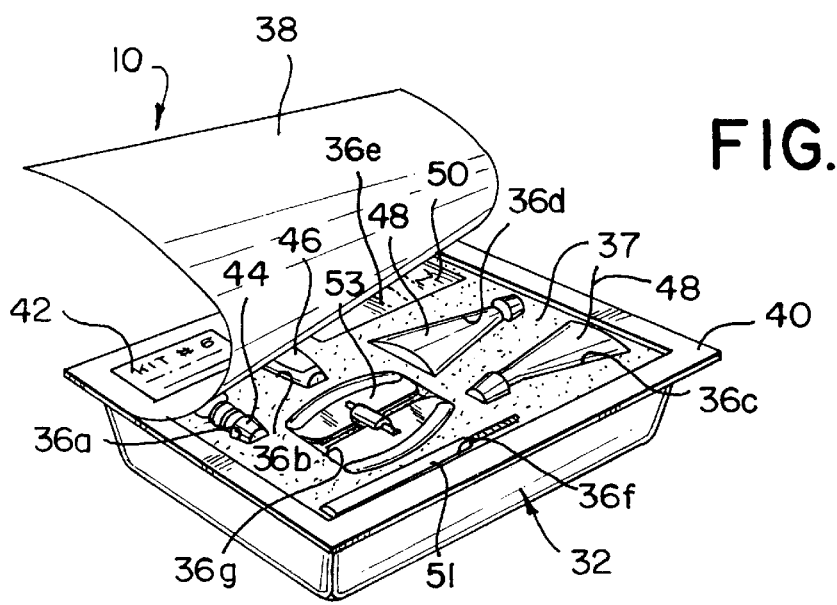
FIG. 4 is an isometric view of a representative kit with a removable cover partially opened.

Referring now to FIGS. 2–4, each kit 10 includes a portable housing or package 32. The configuration of the package 32 may be varied and is not critical to the invention. In an exemplary embodiment, package 32 contains a molded plastic body 34 defining plurality of compartments 36a, 36b, 36c, 36d, 36e, 36f and 36g. The number of compartments depends on the number of components to be stored in the kit. In the illustrative embodiment, each compartment is formed as a depression in a foam or preformed plastic insert 37 to receive the particular component to be stored in that compartment in accordance with common practice. A thin transparent or translucent plastic sheet 38 extends over the top of the body 14 and is sealed to the flange 40 in a conventional manner to maintain sterility. When the kit 10 is ready for use, the plastic sheet 38 is pulled away from the flange 40 to expose the individual compartments in the package 32. Each kit 10 is uniquely identified with one of the dental areas as discussed above by indicia 42 on the package 32. In this manner, the dentist or dental assistant can readily procure the proper kit 10 for the particular dental area in which post-extraction procedures are to be implemented. Each kit 10 includes a dental implant 44 of specified dimensions for the target dental area, a transfer coping 46 attachable to the dental implant for creating an impression (for making a model to produce a prosthetic tooth), a bone graft material syringe 48 for depositing bone graft material 66 for filling in an area around a portion of the implant after implantation, a wound dressing 50, a burr 51 and bone expander 53. As shown in FIG. 8, the syringe 48 includes a plastic or glass body 68, a plunger 70 and a hydrating blood tip 64. If desired, additional components can be added by providing the package 32 with a greater number of compartments. Alternatively, fewer components can be packaged in the kit by providing the package with a smaller number of compartments.

The component which is differentiated between the kits 10 is the dental implant 44. Each dental area requires a dental implant 44 of a particular length and width. Typical implants are screw-type titanium implants such as those disclosed in Linkow et al. U.S. Pat. No. 3,499,222, the disclosure of which is hereby incorporated by reference. Additional "screw" and "press-fit" implants, e.g., HA and non-HA coated cylinder implants, are made by numerous dental implant companies, including Bicon™, STRAUMANN®, CALCITEK, NOBELBIOICARE, 3I and others. These implants may be buried in the alveolar ridge crest bone of the patient in an edentulous region. The implant has a threaded lower portion that may be screwed into an opening created in the bone after the tissue has been displaced (single stage implant). Other implants known as two-stage implants are submergible and can be completely embedded in the bone, such as those disclosed in Linkow et al. U.S. Pat. No. 4,713,004, the disclosure of which is hereby incorporated by reference (see above). These are covered with tissue after grafting and allowed to remain in place while new bone grows around the implant and through vent holes in the implant. After the implant is firmly anchored in new bone, the tissue is reopened and an upper post portion (abutment) is screwed into the implant portion and used to mount the artificial tooth. Implants having conical or U-shaped profiles are disclosed in Linkow U.S. Pat. No. 4,521,192 and Sprague U.S. Pat. No. 2,609,604, the disclosures of which are hereby incorporated by reference. Exemplary commercially available implants come in representative sizes such as 3.5mm by (8.0mm, 11.0mm, and 14.0mm); 4.0mm by (8.0mm, 11.0mm, or 14.0mm); and 5.0mm by (8.0mm, 11.0mm, or 14.0mm). If a particular kit 10 contains an implant for a target area which is too small because of the size and geometry of the patient's one structure, the next largest implant from a kit 10 for another area may be used. The bone graft material 66 is used to fill in a void area around a portion of the implant as well as building out the buccal-lingual diameter of the jawbone after implantation. Such bone graft material includes bovine (xenographic) bone, synthetic bone (alloplastic, e.g., ceramic orplastic), allographic bone, or combinations thereof. This material may be resorbable or non-resorbable, solid or microporous. An exemplary synthetic bone material is disclosed in Ashman et al. U.S. Pat. No. 4,728,570, and sold under the tradename Bioplant® HTR®.

A transfer coping 46 attachable to the implant 44 for creating an impression for making a model to produce a prosthetic tooth is provided in each kit 10. Examples of transfer copings may be found in U.S. Pat. Nos. 4,911,811 and 5,685,715, the disclosures of which are hereby incorporated by reference. Exemplary commercially available transfer copings can be obtained from Bicon® or STAUMANN®.

Figure 5:
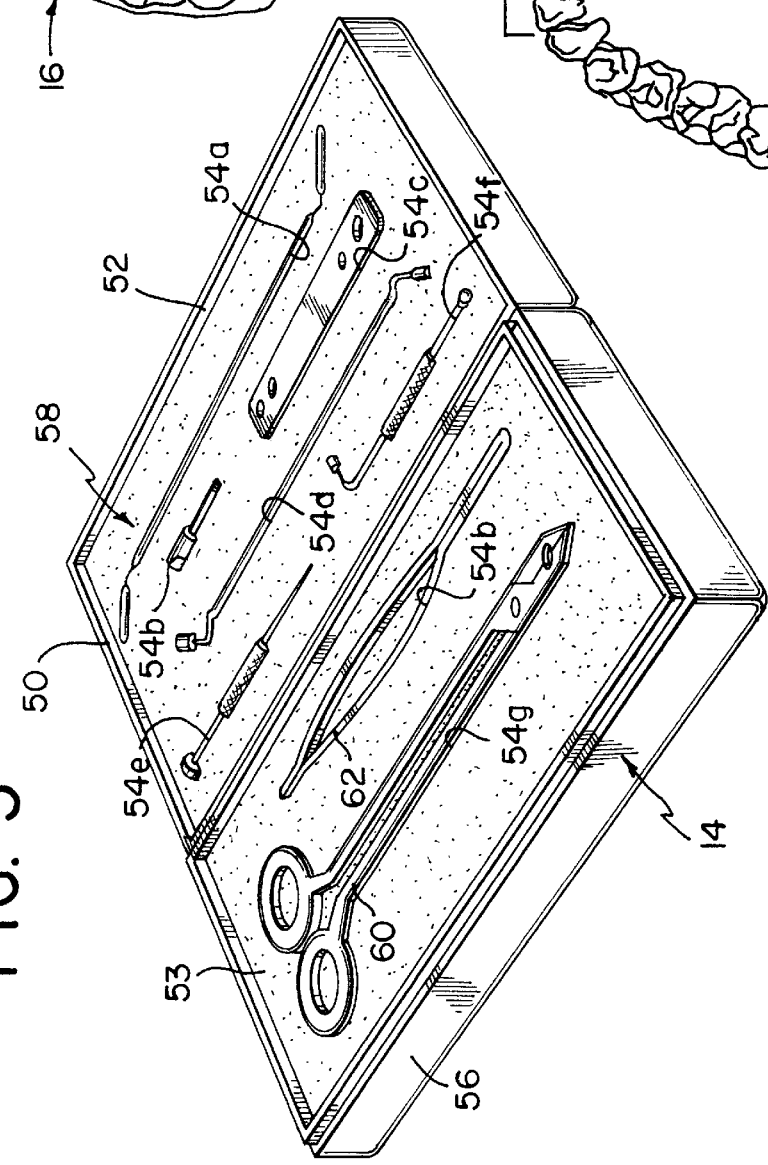
FIG. 5 is an isometric view of an instrument kit.

The instrument kit 14 is reusable, and includes a plurality of sterilizable components for implementing the post extraction implantation procedure. Referring now to FIG. 5, each instrument kit 14 includes a housing or package 50. Like the disposable kit 10, the configuration of the package 50 may be varied and is not critical to the invention. In an exemplary embodiment, package 50 contains a molded plastic body 52 and a foam insert 53 having a plurality of molded depressions which respectively define a plurality of compartments 54a, 54b, 54c . . . 54h. The number of compartments depends on the number of components to be stored in the kit. A hinged cover 56 extends over the top of the body 52 in a conventional manner. When the kit 14 is ready for use, the cover 56 is opened from the body 52 to expose the individual compartments in the package 50. The kit 14 includes insertion instruments generally indicated by the reference numeral 58, a scissor 60 and a suture holder 62. The insertion instruments 58 may include drills, burrs, bone expanders, reamers, paralleling pins, depth gauges, implant inserters, healing plug cutters, implant/abutment seating tips, bone graft pluggers, threaded knobs, threaded handles, reamer attachments, abutment seating tips, implant retrievers and the like. These items are commercially available from a source such as, for example, STRAUNN®. The components in the instrument kit 14 may be sterilized and reused after the immediate post-extraction procedure is completed. Each kit with the implant(s) and graft material, etc., is adapted for single-use only and disposable.

In accordance with the present invention, there is also provided a method for immediate post-extraction implantation of dental implants, comprising the steps of: immediately after extraction, removing from a kit adapted for a particular dental area of the mouth, a dental implant of specified dimensions for the particular dental area of the mouth, and inserting the dental implant into an extraction socket; removing a transfer coping and a protectant dressing (e.g., Biofoil™) from the kit, and attaching the transfer coping to the dental implant to make a model to produce a prosthetic tooth, and placing the protectant dressing over the surgical area for healing protection. The method may further comprise the step of removing a bone graft material from the kit and filling a void area around a portion of the implant after implantation.

The present invention has been shown and described in what are considered to be the most practical and preferred embodiments. It is anticipated, however, that departures can be made there from and that obvious modifications will be implemented by persons skilled in the art.

What is claimed is:

1. A disposable kit for implementing immediate post-extraction dental implantation, comprising:
    a portable housing storing a plurality of components for said implantation, said components including
        a dental implant of specified dimensions for a particular dental area;
        a transfer coping attachable to said dental implant for creating an impression for making a model to produce a prosthetic tooth; and
        bone graft material for filling a void area around a portion of said implant after implantation.

2. The kit recited in claim 1, wherein said components further include a wound dressing.

3. The kit recited in claim 1, wherein said housing includes a plurality of compartments and each of said compartments contains one of said components.

4. The kit recited in claim 1, wherein said components further include a bone graft material syringe, a burr, and a bone expander.

5. A disposable kit for implementing immediate post-extraction dental implantation, comprising:
    a portable housing storing;
    a dental implant of a specified size for a particular dental area;
    a transfer coping attachable to said dental implant for creating an impression for making a model to produce a prosthetic tooth;
    bone graft material for filling a void area around a portion of said implant after implantation; and
    a wound dressing.

6. A kit system comprising a kit system housing containing a plurality of disposable kits, each kit being adapted for post-extraction dental implantation on a particular dental area and comprising:
    a portable housing storing a plurality of components for said implantation, said components including
        a dental implant of a specified size for a particular dental area;
        a transfer coping attachable to said dental implant for creating an impression for making a model to produce a prosthetic tooth;
        bone graft material for filling a void area around a portion of said implant after implantation; and
        a wound dressing.

7. The kit system recited in claim 6, further comprising a non-disposable instrument kit including an instrument housing storing a plurality of reusable and sterilizable tools for implementing said post-extraction dental implantation.

8. The kit system recited in claim 7, wherein said tools include insertion instruments, a scissor, and a suture holder.

9. The kit system recited in claim 6, further comprising indicia associated with each disposable kit identifying said particular dental area for said implant in said each kit.

10. A method of using the kit system of claim 6, comprising the steps of: immediately after extraction of a tooth from a particular dental area of the mouth, selecting a kit from the kit system having an implant stored therein that is suitable for use in the particular dental area, removing the implant therefrom, and inserting the dental implant into the extraction socket resulting from the extraction of the tooth.

11. The method recited in claim 10, further comprising the steps of removing the transfer coping from the kit, and attaching the transfer coping to the dental implant to make a model to produce a prosthetic tooth.

12. The method recited in claim 11, further comprising the steps of removing the bone graft material from the kit and filling therewith any void area around the implant after implantation.

* * * * *